United States Patent [19]

Breipohl et al.

[11] Patent Number: 5,817,811
[45] Date of Patent: Oct. 6, 1998

[54] PROCESS FOR PREPARING SUBSTITUTED N-ETHYGLYCINE DERIVATIVES

[75] Inventors: Gerhard Breipohl, Frankfurt; Eugen Uhlmann, Glashütten; David William Will, Eschborn, all of Germany

[73] Assignee: Hoechst Aktiengesellschaft, Frankfurt am Main, Germany

[21] Appl. No.: 707,149

[22] Filed: Sep. 3, 1996

[30] Foreign Application Priority Data

Sep. 4, 1995 [DE] Germany .................. 195 32 553.2

[51] Int. Cl.⁶ ............... C07D 473/00; C07D 487/00; C07D 239/02
[52] U.S. Cl. ............. 544/264; 544/244; 544/265; 544/276; 544/277; 544/280; 544/311; 544/312; 544/317
[58] Field of Search ................ 544/244, 264, 544/265, 276, 277, 280, 311, 312, 317

[56] References Cited

FOREIGN PATENT DOCUMENTS

0688766A1  12/1995  European Pat. Off. .

OTHER PUBLICATIONS

Meltzer et al., Peptide Nucleic Acids: Synthesis of Thymine, Adenine Guanine, and Cytosine Nucloebases, The Journal of Organic Chemistry, vol. 60, No. 13, pp. 4305–4308, Jun. 1995.

Finn et al., Synthesis and Properties of DNA–PNA Chimeric Oligomers, Nucleic Acids Research, vol. 24, No. 17, pp. 3357–3363, Sep. 1996.

Breipohl et al., Synthesis of Polyamide Nucleic Acids (PNAs) Using a Novel Fmoc/Mmt Protecting–Group Combination, Bioorganic & Medicinal Chemistry Letters, vol. 6, No. 6, pp. 665–670, Mar. 1996.

Will et al., The Sythesis of Polyamide Nucleic Acids Using a Novel Monomethoxytrityl Protecting–Group Strategy, Tetrahedron, vol. 51, No. 44, pp. 12069–12082, Oct. 1995.

Dueholm et al., Synthesis of Peptide Nucleic Acid Monomers Containing the Four Natural Nucleobases: Thymine, Cytosine, Adenine, and Guanine and Their Oligomerization, The Journal of Organic Chemistry, vol. 59, No. 19, pp. 5767–5773, Sep. 1994.

Egholm et al., Peptide Nucleic Acids Containing Adenine or Guanine Recognize Thymine and Cytosine in Complementary DNA Sequences, Journal of the Chemical Society Chemical Communications, No. 9, pp. 800–801, May 1993.

J. Jones, The Chemical Synthesis of Peptides, Clarendon Press, Oxford, England, pp. 17–18; 22–23; 26–27; and 33–35, (1991).

S.A. Thompson et al., "Fmoc Mediated Synthesis of Peptide Nucleic Acids," Tetrahedron, vol. 51, No. 22, pp. 6179–6194 (1995).

J. Coste, et al., "PyBOP®: A New Peptide Coupling Reagent Devoid of Toxic By Product", Tetrahedron Letters, vol. 31, No. 2, pp. 205–208, (1990).

J. Coste et al., "BROP: A New Reagent for Coupling N–Methylated Amino Acids", Tetrahedron Letters, vol. 31, No. 5, pp. 669–672, (1990).

J. Coste, et al., "Oxbenzotriazole Free Peptide Coupling Reagents for N–Mehtylated Amino Acids", Tetrahedron Letters, vol. 32, No. 17, pp. 1967–1970, (1991).

V. Dourtogolou et al., "O–Benzotriazolyl–N, N, N', N'–tetramethyluronium Hexafluorophosphate as Coupling Reagent for the Synthesis of Peptides of Biological Interest", Synthesis, pp. 572–574, (1984).

R. Knorr et al, "New Coupling Reagents in Peptide Chemistry", Tetrahedron Letters, Vlol. 30, No. 15, pp. 1927–1930, (1989).

L.A. Carpino, "1–Hydroxy–7–azabenzotriacole. An Effcient Peptide Coupling Additive", J. Am. Chem. Soc., 115, pp. 4397–4398, (1993).

A. Ehrlich et al., "Synthesis of Cyclic Peptides via Efficient New Coupling Reagents", Tetrahedron Letters, vol. 34, No. 30, pp. 4781–4784, (1993).

Kenich Akaji et al., "Anchoring of Fmoc Amino Acid to 4–Alkoxybenzyl alchol Resing using a New Esterification Reagent", Tetrahedron Letters, vol. 33, No. 22, pp. 3177–3180, (1992).

Louis A. Carpino et al., "((9–Fluroenylmethyl)oxy) carbonyl Amino Acid Chlorides in Solid–Phase Peptide Synthesis", J. Org. Chem, 45, pp. 26–35–2642, (1991).

Jean–Noel Bertho et al., "Preparation and use of N–protected amino acid flurides in peptide synthesis", E. Giralt and D. Andreu (Eds.), Peptides 1990, Escom Science Publisher B. V., pp. 53–54 (1991).

Jeremy Green et al., "Studies on the Acylation of Hydroxy–Functionalized Resins Using Fmoc Amino Acids Activated Using Diisopropylcarbodiimide/HOBt or as Acids Fluorides", Tetrahedron Letters, vol. 49, No. 20, pp. 4141–4146, (1993).

Birgit Blankemeyer–menge et al., "An Efficient Method for Anchoring FMOC–Amino Acids to Hydroxyl–Functionalised Solid Supports", Tetrahedron Letters, vol. 31, No. 12, pp. 1701–1704, (1990).

(List continued on next page.)

Primary Examiner—Mukund J. Shah
Assistant Examiner—Brenda Coleman
Attorney, Agent, or Firm—Finnegan, Henderson, Farabow, Garrett & Dunner, L.L.P.

[57] ABSTRACT

Processes are described for preparing substituted N-ethylglycine derivatives of the formula

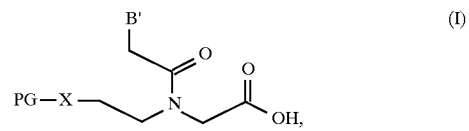

in which PG is an amino protecting group which is labile towards weak acids and is of the urethane type or the trityl type, X is NH or O, and B' represents bases which are customary in nucleotide chemistry and whose exocyclic amino and/or hydroxyl groups are protected by suitable known protecting groups, and the salts thereof.

15 Claims, No Drawings

OTHER PUBLICATIONS

Derek Hudson, "Methodological Implications of Simultaneous Solid–Phase Peptide Synthesis: A Comparison of Active Esters", Peptides Research, pp. 51–55, (1990).

John E. Bishop et al., "The Reaction of Thioimides with Phosphorus Ylides", J. Org. Chem., 56, pp. 5079–5091, (1991).

A. Paul Krapcho et al., "Mono–Protected Diamines, N–tert–BUTOXYCARBONYL–$_{a,w}$–Alkanediamines from $_{a,w}$–Alkanediamines", Synthetic Communications, 20(16), pp. 2259–2564, (1990).

Antonio Evidente et al., "Syntheses of cis–Zeatin and Its 9–(Dexy–β–D–ribofuranosyl) Derivative: A Novel Synthetic Route to the Side Chain at C(6), and Cytokinin Acitivity", Chem. Pharm. Bull 40(7), pp. 1937–1939, (1992).

PROCESS FOR PREPARING SUBSTITUTED N-ETHYGLYCINE DERIVATIVES

The present invention relates to a novel, improved process for preparing substituted N-ethylglycine derivatives, for the synthesis of PNA and PNA/DNA hybrids, which are described in EP-A 672 661. These substituted N-ethylglycine derivatives are used to prepare the PNA and PNA/DNA hybrids which are described in EP-A 672 677. Their application relates to their use as inhibitors of gene expression (antisense oligonucleotides, ribozymes, sense oligonucleotides and triplex-forming oligonucleotides), as probes for detecting nucleic acids, and as aids in molecular biology.

The object of the invention is to find a simple and economical process for preparing these substituted N-ethylglycine derivatives.

The novel process for preparing the substituted N-ethylglycine derivatives of the formula I

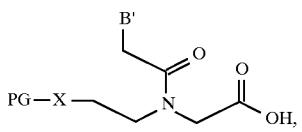

in which
PG is an amino protecting group which is labile towards weak acids and is a urethane derivative, for example 1-(1-adamantyl)-1-methylethoxycarbonyl (Adpoc), 1-(3,5-di-tert-butylphenyl)-1-methylethoxycarbonyl (t-Bumeoc), 1-methyl-1-(4-biphenyl)ethyloxycarbonyl (Bpoc), tert-butyloxycarbonyl (Boc) or 3,5-dimethoxyphenyl-2-propyl-2-oxycarbonyl (Ddz), or a triphenylmethyl derivative such as the triphenylmethyl (Trt), (4-methoxyphenyl)diphenylmethyl (Mmt), (4-methylphenyl)diphenylmethyl (Mtt), di-(4-methoxyphenyl)phenylmethyl (Dmt), or 9-(9-phenyl)xanthenyl (pixyl) radical, X is NH or O, and B' represents nucleo bases, which are customary in nucleotide chemistry, for example natural, i.e. naturally occurring, bases such as adenine, cytosine, guanine, thymine and uracil, or unnatural, i.e. synthetic, bases, such as purine, 2,6-diaminopurine, 7-deazaadenine or 7-deazaguanine, both of the latter of which are optionally substituted in the 7-position by a substituent from the group consisting of halogen, preferably chlorine, bromine or iodine, $(C_1-C_{10})$-alkyl, preferably $(C_3-C_6)$-alkyl, $(C_2-C_{10})$-alkenyl, preferably $(C_3-C_6)$-alkenyl, and $(C_3-C_{10})$-alkynyl, preferably [chlorine, bromine or iodine, $(C_3-C_6)$-alkyl, $(C_3-C_6)$-alkenyl or] $(C_3-C_6)$-alkynyl, $N^4N^4$-ethanocytosine, $N^6N^6$-ethano-2,6-diaminopurine, 5-methylcytosine, 5-$(C_3-C_6)$-alkynyluracil, 5-$(C_3-C_6)$-alkynylcytosine, 5-fluorouracil or pseudoisocytosine, whose exocyclic amino and/or hydroxyl groups are protected by suitable, known protecting groups, such as the benzoyl, isobutanoyl, acetyl, phenoxyacetyl, 4-(t-butyl)benzoyl, 4-(t-butyl)phenoxyacetyl, 4-(methoxy)benzoyl, 2-(4-nitrophenyl)ethyloxycarbonyl, 2-(2,4-dinitrophenyl)ethyloxycarbonyl, 9-fluorenylmethoxycarbonyl, diphenylcarbamoyl or formamidine group, preferably the benzoyl, isobutanoyl, acetyl, phenoxyacetyl, 4-(t-butyl)benzoyl or 4-(methoxy)benzoyl group, and, for guanine, also by a combination of 2-N-acetyl and 6-O-diphenylcarbamoyl groups, or their salts, preferably their salts with tert organic bases, for example triethylamine or pyridine, comprises
a) reacting a compound of the formula II

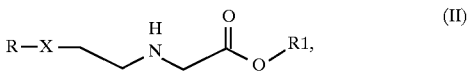

in which
R is hydrogen or, when X=NH, an acid-labile protecting group, for example Boc, Ddz or Trt, preferably Boc, and $R^1$ is a protecting group which is labile towards acids and stable towards amines, for example the tert-butyl and (2-chlorophenyl)diphenylmethyl groups, preferably the tert-butyl group, and X is defined as above, with a compound of the formula III

in which
B' is defined as above, at 0°–45° C., preferably at room temperature, in a suitable solvent, for example DMF, acetonitrile or dichloromethane or mixtures of the solvents, using a coupling reagent which is customary in peptide chemistry, for example carbodiimides, phosphonium reagents, uronium reagents, acid halides or activated esters, to give a compound of the formula IV

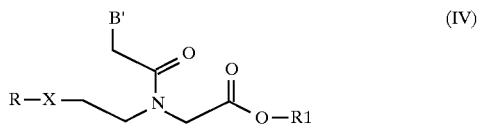

in which
R, X, B' and $R^1$ are as defined above;

b) subsequently converting the compound of the formula IV, by means of eliminating the acid-labile ester protecting group $R^1$ and, for X=NH, by means of simultaneously eliminating the acid-labile protecting group R, under suitable acidic conditions using, for example, trifluoroacetic acid in a suitable solvent, for example dichloromethane, ethylacetate, dioxane, etc., where appropriate with the addition of cation-capturing agents, for example anisole, thiophenol, triethylsilane, etc., into a compound of the formula V, with it being possible, in the case of compounds of the formula IV in which X=O, for the lactone of the formula Va also to be formed to a certain extent during the course of this elimination, which lactone can, however, be readily converted, by treatment with bases, for example NaOH or triethylamine in aqueous medium, into the open-chain derivative of the formula V,

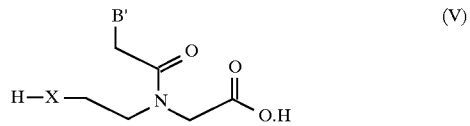

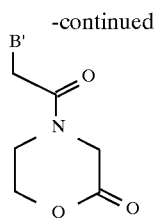

(Va)

in which

X and B' are defined as above; and c) converting the compound of the formula V, by introducing therein the amino protecting group PG, using a suitable reagent, for example t-Bumeoc fluoride, Adpoc azide, Bpoc azide, Ddz (phenyl)carbonate, Trt-Cl, Mtt-Cl, Mmt-Cl, Dmt-Cl or Pixyl-Cl, in a suitable solvent, for example DMF, NMP, acetonitrile, dichloromethane, or mixtures of these solvents, using an auxiliary base, for example NEM, DIPEA, pyridine or triiethylamine, into the compound of the formula I and subsequently, where appropriate, converting the latter into its salts.

Activation methods which are customary in peptide synthesis are described, for example, in Houben-Weyl, Methoden der organischen Chemie [Methods of organic chemistry], Volume 15/2, while additional reagents, for example BOP (B. Castro, J. R. Dormoy, G. Evin and C. Selve, Tetrahedron Lett. 1975, 1219–1222), PyBOP (J. Coste, D. Le-Nguyen and B. Castro, Tetrahedron Lett. 1990, 205–208), BroP (J. Coste, M.-N. Dufour, A. Pantaloni and B. Castro, Tetrahedron Lett. 1990, 669–672), PyBroP (J. Coste, E. Frerot, P. Jouin and B. Castro, Tetrahedron Lett. 1991, 1967–1970) and uronium reagents, for example HBTU (V. Dourtoglou, B. Gross, V. Lambropoulou, C. Zioudrou, Synthesis 1984, 572–574), TBTU, TPTU, TSTU, TNTU, (R. Knorr, A. Trzeciak, W. Bannwarth and D. Gillessen, Tetrahedron Letters 1989, 1927–1930), TOTU (EP-A-0 460–446), HATU (L. A. Carpino, J. Am. Chem. Soc. 1993, 115, 4397–4398), HAPyU, TAPipU (A. Ehrlich, S. Rothemund, M. Brudel, M. Beyermann, L. A. Carpino and M. Bienert, Tetrahedron Lett. 1993, 4781–4784), BOI (K. Akaji, N. Kuriyama, T. Kimura, Y. Fujiwara and Y. Kiso, Tetrahedron Lett. 1992, 3177–3180), propanephosphonic anhydride (PPA) (H. Wissmann, H. J. Kleiner, Angew. Chem. 92, 129–130, 1990) or acid chlorides or acid fluorides (L. A. Carpino, H. G. Chao, M. Beyermann and M. Bienert, J. Org. Chem., 56(1991), 2635; J.-N. Bertho, A. Loffet, C. Pinel, F. Reuther and G. Sennyey in E. Giralt and D. Andreu (Eds.) Peptides 1990, Escom Science Publishers B. V.1991, pp. 53–54; J. Green and K. Bradley, Tetrahedron 1993, 4141–4146), 2,4,6-mesitylenesulfonyl-3-nitro-1,2,4-triazolide (MSNT) (B. Blankemeyer-Menge, M. Nimitz and R. Frank, Tetrahedron Lett. 1990, 1701–1704), 2,5-diphenyl-2,3-dihydro-3-oxo-4-hydroxythiophene dioxide (TDO) (R. Kirstgen, R. C. Sheppard, W. Steglich, J. Chem. Soc. Chem. Commun. 1987,1870–1871) or activated esters (D. Hudson) Peptide Res. 1990, 51–55) are described in the respective literature sources.

The use of carbodiimides, for example dicyclohexylcarbodiimide or diisopropylcarbodiimide, is preferred. Preference is also given to the use of phosphonium reagents, for example PyBOP or PyBroP, to uronium reagents, for example HBTU, TBTU, TPTU, TSTU, TNTU, TOTU or HATU, to BOI or to acid chlorides or acid fluorides, and to propanephosphonic anhydride (PPA).

The advantage of the novel process for preparing the compounds of the formula I in which X=NH is that the protecting groups for the primary amino function and the carboxyl group of the aminoethylglycine are eliminated simultaneously from the intermediate of the formula IV by the action of a single reagent, for example trifluoroacetic acid. The compound of the formula I is then formed directly by introducing the protecting group PG. The advantage for preparing the title compounds of the formula I in which X=O is that the protection of the carboxyl group improves the solubility of the hydroxyethylglycine derivative in organic solvents, on the one hand, and facilitates linkage to compounds of the formula II, on the other.

Synthesis of the compounds of the formula II is effected, for example, by reacting commercially obtainable 1,2-diaminoethane or aminoethanol with the appropriate haloacetic ester, for example commercially available tert-butyl chloroacetate or tert-butyl bromoacetate. For X=NH and R=acid-labile protecting group, there then follows a reaction of the aminoethylglycine ester with a suitable protecting group reagent, for example Ddz-(phenyl) carbonate, Trt-Cl, di-tert-butyl dicarbonate, Boc-ONSu or tert-butylphenyl carbonate. A further process comprises reacting monoprotected 1,2-diaminoethane, for example mono-Boc-diaminoethane, with haloacetic esters, for example tert-butyl chloroacetate or tert-butyl bromoacetate.

Another process for preparing the compounds of the formula II in which R =Boc and $R^1$=tert-butyl is the reductive amination of tert-butyl glyoxilate with ethylenediamine, mono-Boc-ethylenediamine (for X=NH) or aminoethanol (for X=O) using hydrogen on palladium on carbon, or using sodium cyanoborohydride or sodium triacetoxyborohydride, as the reducing agent. The tert-butyl glyoxylate which is required for this reaction can be obtained as described, for example, in J. E. Bishop, J. F. O'Connell and H. Rapoport, J. Org. Chem. 1991, 5079–5091 the synthesis of mono-Boc-ethylenediamine is described, for example, in Kapcho, A. P. and Kuell, C. S., Synth Commun. (1990), 2559–2564.

The reductive amination of Boc-glycinal with glycine tert-butyl ester using hydrogen on palladium on carbon, or using sodium cyanoborohydride or sodium triacetoxyborohydride, as the reducing agent, is likewise suitable for preparing compounds of the formula II in which X=NH. The Boc-glycinal which is required for this purpose is prepared as described, for example, in A. Evidente, G. Picalli, A. Sisto, M. Ohba, K. Honda, T. Fujii, Chem. Pharm. Bull. 1992, 1937–1939; glycine tert-butyl ester is commercially available.

The nucleotide base-acetic acid derivatives of the formula III can be obtained by alkylating the corresponding nucleotide bases, or the nucleotide bases which are protected in their exocyclic hydroxyl or amino function, with chloroacetic acid, bromoacetic acid, iodoacetic acid or their esters. In this context, additional, temporary protecting groups are introduced on the nucleotide base in order to ensure selective alkylation. All the protecting groups which are compatible with the protecting group PG, which is labile towards weak acids, may be used for the protecting group for the nucleotide bases. Protecting groups such as the benzoyl, isobutanoyl, acetyl, phenoxyacetyl, 4-(t-butyl)benzoyl, 4-(t-butyl)phenoxyacetyl, 4-(methoxy)benzoyl, 2-(4-nitrophenyl)ethyloxycarbonyl, 2-(2,4-dinitrophenyl)ethyloxycarbonyl, 9-fluorenylmethoxycarbonyl or formamidine groups are preferably used for the exocyclic amino function. Those which are particularly preferred are the benzoyl, isobutanoyl, 4-(t-butyl)benzoyl, 2-(4-nitrophenyl)ethyloxycarbonyl, 2-(2,4-dinitrophenyl)ethyloxycarbonyl, 9-fluorenylmethoxycarbonyl, 4-(methoxy)benzoyl or para-(t-butyl)phenoxyacetyl or para-nitrophenyl-2-ethyloxycarbonyl groups.

The invention furthermore relates to the valuable intermediates of the formula IV, in which R, X, B' and $R^1$ are

EXAMPLES

Example 1

Hydroxyethylglycine tert-butyl ester (H-Oeg-OtBu)

30.2 ml (0.5 mol) of aminoethanol were dissolved in 200 ml of DMF, and 17 ml (0.1 mol) of diisopropylethylamine were added, followed by 14.8 ml (0.1 mol) of tert-butyl bromoacetate, which was added dropwise. The mixture was stirred at room temperature for 24 h and the solvent was then evaporated off in vacuo on a rotary evaporator. The residue was taken up in 100 ml of water, and this solution was saturated with sodium chloride and then extracted with 3 times 100 ml of ethyl acetate. The organic phase was washed with a small quantity of a saturated solution of NaCl, dried over sodium sulfate and then evaporated to dryness. 11.96 g of the product were obtained as a colorless oil.

MS(ES$^+$): 176.2 (M+H)$^+$

R$_f$=0.51 (2-butanone:water:pyridine:acetic acid/70:15:15:2)

Example 1A

Hydroxyethylglycine tert-butyl ester (H-Oeg-OtBu)

3 ml (0.05 mol) of aminoethanol were dissolved in 20 ml of DMF, and 1.7 ml (0.01 mol) of diisopropylethylamine were added followed by 1.4 ml (0.01 mol) of tert-butyl chloroacetate, which was added dropwise. The mixture was stirred at room temperature for 24 h and the solvent was then evaporated off in vacuo on a rotary evaporator. The residue was taken up in 20 ml of water, and this solution was saturated with sodium chloride and then extracted with three times 20 ml of ethyl acetate. The organic phase was washed with a small quantity of a saturated solution of NaCl, dried over sodium sulfate and then concentrated to dryness. 1.9 g of the product were obtained as a colorless oil.

MS(ES$^+$): 176.2 (M+H)$^+$

R$_f$=0.51 (2-butanone:water:pyridine:acetic acid/70:15:15:2)

Example 2

N-(Hydroxy)ethyl-N-((1-thyminyl)acetyl)glycine tert-butyl ester (H-Oeg(T)-OtBu)

8.9 g (53 mmol) of H-Oeg-OtBu were dissolved in 100 ml of DMF, and 8.8 g (48 mmol) of thyminylacetic acid, 19.4 ml (106 mmol) of triethylamine and 17.4 g (53 mmol) of TOTU were then added in succession. The mixture was stirred at room temperature for a further 3 h and the solvent was then evaporated off in vacuo on a rotary evaporator. The residue was stirred up with a little ethyl acetate, whereupon the product began to precipitate out. The mixture was then left to stand at 4° C. overnight, after which the precipitated product was filtered off with suction, then washed with a little ethyl acetate and dried in vacuo. Yield: 11.8 g of a colorless substance.

MS(ES$^+$): 342.2 (M+H)$^+$

R$_f$=0.75 (2-butanone:water:pyridine:acetic acid/70:15:15:2)

Example 3

N-(Hydroxy)ethyl-N-((1-thyminyl)acetyl)glycine (H-Oeg(T)-OH)

9.47 g (28 mmol) of H-Oeg(T)-OtBu were suspended in 150 ml of dichloromethane, and 100 ml of 95% trifluoroacetic acid (5% water) are added. A clear solution was formed which was then stirred at room temperature for 3 h. The reaction mixture was then added dropwise to 1 l of cold (0° C.), thoroughly stirred methyl tert-butyl ether, whereupon the product precipitated out. The precipitated crude product (also containing a little lactone which had been formed) was dissolved in a mixture comprising 170 ml of dioxane, 170 ml of water and 6.4 ml of triethylamine, and the whole was stirred at room temperature for 2 h, in association with which the lactone was opened and the triethylammonium salt was formed. The mixture was then evaporated to dryness and the residue was dried in vacuo.

Yield: 10.51 g of amorphous solid

MS(ES$^+$): 286.2 (M+H)$^+$

R$_f$=0.12 (dichloromethane:methanol:ethylacetate/10:2:1 and 1% triethylamine)

Example 4

N-(Di-(4-methoxyphenyl)phenylmethyloxy)ethyl-N-((1-thyminyl)acetyl)glycine (Dmt-Oeg(T)-OH)

1.0 g (2.6 mmol) of H-Oeg(T)-OHNEt$_3$ were dissolved in 10 ml of DMF, and 1.4 ml (10 mmol) of triethylamine were added. 1.8 g (5.2 mmol) of Dmt-Cl in 10 ml of dichloromethane were then added dropwise, and the mixture was stirred at room temperature for 16 h. The solvent was then evaporated off in vacuo on a rotary evaporator and the residue was taken up in dichloromethane; This latter solution was washed with water and the organic phase was then dried over sodium sulfate and evaporated. The resulting crude product was purified by means of column chromatography on silica gel using dichloromethane/methanol/ethyl acetate 15:1:1 containing 1 % triethylamine as the eluent. The fractions containing the product were combined and concentrated. 960 mg of the product were obtained as a foam.

MS(FAB, MeOH/NBA): 587.3 (M)$^+$

R$_f$=0.29 (dichloromethane:methanol:ethyl acetate/10:2:1 and 1% triethylamine)

Example 5

N-(Hydroxy)ethyl-N-((1-(N$^4$-(4-tert-butylbenzoyl)cytosyl)acetyl)glycine tert-butyl ester (H-Oeg(C$^{MeoBz}$)-OtBu)

1.8 g (11 mmol) of H-Oeg-OtBu were dissolved in 100 ml of DMF, after which 3.0 g (10 mmol) of N$^4$-(4-methoxybenzoyl)-N$^1$-carboxymethylcytosine, 3 ml of triethylamine and 3.6 g (11 mmol) of TOTU were added in succession. The reaction mixture was stirred at room temperature for a further 4 h and the solvent was then evaporated of in vacuo on a rotary evaporator. The residue was taken up in ethyl acetate, and this solution was washed twice with a solution of sodium hydrogen carbonate. In association with this, the product precipitated out in the ethyl acetate phase. The precipitated product was filtered off with suction, then washed with a little ethyl acetate and dried in vacuo. Yield: 3.06 g of a colorless substance.

MS(FAB, MeOH/NBA): 461.3 (M+H)$^+$

R$_f$=0.81 (2-butanone:water:pyridine:acetic acid/70:15:15:2)

Example 6

N-(Hydroxy)ethyl-N-((1-(N$^4$-(4-tert-butylbenzoyl)cytosyl)acetyl)glycine (H-Oeg($C^{MeOBz}$)-OH)

1.5 g (3.4 mmol) H-Oeg($C^{MeoBz}$)-OtBu were dissolved in a mixture comprising 30 ml of dichloromethane and 20 ml of 95% trifluoroacetic acid (5% water) which contained 2.5 ml of anisole. The clear solution was stirred at room temperature for 5h and then added dropwise to 500 ml of cold (0° C.), thoroughly stirred methyl tert-butyl ether, whereupon the product precipitated out. The precipitated crude product (also containing a little lactone which had been formed) was dissolved in a mixture comprising 25 ml of dioxane, 25 ml of water and 0.44 ml of triethylamine, and this solution was stirred at room temperature for 3h, in association with which the lactone was opened and the triethylammonium salt was formed. The mixture was then evaporated to dryness and the residue was purified by means of column chromatography on silica gel using dichloromethane/methanol/ethyl acetate 10:3:2 containing 1% triethylamine as the eluent.

Yield: 920 mg of an amorphous solid

MS($ES^+$): 405.2 $(M+H)^+$ $R_f$=0.16 (dichloromethane:methanol:ethyl acetate/10:3:2 and 1% triethylamine)

Example 7

N-(Di-(4-methoxyphenyl)phenylmethyloxy)ethyl-N-((1-($N^4$-(4-methoxybenzoyl)cytosyl)acetyl)glycine (Dmt-Oeg($C^{MeBz}$)-OH)

920 mg (1.8 mmol) of H-Oeg($C^{MeBz}$)-OHNEt$_3$ were dissolved in 10 ml of DMF, and 1 ml (7.2 mmol) of triethylamine was added. 1.2 g (3.6 mmol) of Dmt-Cl in 10 ml of dichloromethane were then added dropwise and the mixture was stirred at room temperature for 16 h. The solvent was then evaporated off in vacuo on a rotary evaporator and the residue was taken up in dichloromethane; this solution was washed with water and the organic phase was dried over sodium sulfate and then evaporated. The resulting crude product was purified by means of column chromatography on silica gel using dichloromethane/methanol/ethyl acetate 15:1:1 containing 1% triethylamine as the eluent. The fractions containing the product were pooled and concentrated. 900 mg of the product were obtained as a foam.

MS(FAB, MeOH/NBA): 707.3 $(M+H)^+$ $R_f$=0.24 (dichloromethane:methanol:ethyl acetate/10:3:2 and 1% triethylamine)

Example 8

N-(Hydroxy)ethyl-N-(9-($N^6$-(4-methoxybenzoyl)adenosyl)acetyl)glycine tert-butyl ester (H-Oeg($A^{MeOBz}$)OtBu)

534 mg (3.3 mmol) of H-Oeg-OtBu were dissolved in 10 ml of DMF, after which 1.0 g (3.1 mmol) of $N^6$-(4-methoxybenzoyl)-$N^9$-carboxymethyladenine, 0.77 ml (4.5 mmol) of N-ethylmorpholine and 1.0 g (3.1 mmol) of TOTU were added in succession. The mixture was stirred at room temperature overnight and the solvent was then evaporated off in vacuo on a rotary evaporator. The residue was taken up in ethyl acetate, and this solution was washed twice with a solution of sodium hydrogen carbonate and water. The organic phase was dried over sodium sulfate and then concentrated by evaporation. 1.33 g of the product were obtained.

MS(FAB, MeOH/NBA): 485.3 $(M+H)^+$ $R_f$=0.63 (n-butanol:water:acetic acid/3:1:1)

Example 9

N-(Hydroxy)ethyl-N-(9-($N^6$-(4-methoxybenzoyl)adenosyl)acetyl)glycine (H-Oeg($A^{MeoBz}$)-OH)

1.3 g (2.7 mmol) H-Oeg($A^{MeoBz}$)-OtBu were dissolved in 15 ml of 95% trifluoroacetic acid (5% water). The clear solution was stirred at room temperature for 1 h and was then added dropwise to 250 ml of cold (0° C.), thoroughly stirred diethyl ether, whereupon the product precipitated out. The precipitated crude product (also containing a little lactone which had been formed) was dissolved in a mixture comprising 15 ml of dioxane, 15 ml of water and 0.4 ml of triethylamine, and the whole was stirred at room temperature for 2 h, in association with which the lactone was opened and the triethylammonium salt was formed. The mixture was then evaporated to dryness and the residue was evaporated 3 times, with fuming, with pyridine. The residue was used directly for the next reaction.

MS(FAB, NBA/MeOH/LiCl): 435.2 $(M+Li)^+$ $R_f$=0.37 (n-butanol:water:acetic acid/3:1:1)

Example 10

N-(Di-(4-methoxyphenyl)phenylmethyloxy)ethyl-N-(9-($N^6$-(4-methoxybenzoyl)adenosyl)acetyl)glycine (Dmt-Oeg($A^{MeOBz}$)-OH)

The H-Oeg($A^{MeoBz}$)-OHNEt$_3$ which was obtained in the previous reaction was dissolved in 10 ml of pyridine. 1.7 g (5 mmol) of Dmt-Cl were then added and the mixture was stirred at room temperature for 16 h. The solvent was then evaporated off in vacuo on a rotary evaporator and the residue was taken up in dichloromethane. This solution was washed with 5% aqueous citric acid and a saturated, aqueous solution of NaCl, after which the organic phase was dried over sodium sulfate and then concentrated down to dryness. The resulting crude product was purified by means of column chromatography on silica gel using dichloromethane with a gradient of 1–10% methanol, 1% triethylamine as the eluent. The fractions containing the product were pooled and concentrated. The residue was dissolved in 5 ml of dichloromethane, and this solution was then added dropwise to 100 ml of thoroughly stirred diethyl ether, whereupon the product precipitates out. 580 mg of the product were obtained as a powder.

MS(FAB, MeOH/NBA): 731.3 $(M+H)^+$ $R_f$=0.70 (n-butanol:water:acetic acid/3:1:1)

Example 11

N-(tert-Butyloxycarbonylaminoethyl)glycine tert-butyl ester

Boc-Aeg-OtBu

Step 1:

120 ml (1.8 mol) of 1,2-diaminoethane in 300 ml of dichloromethane were added to a 3-neck flask which was equipped with a stirrer, a reflux condenser and a dropping funnel. 42.7 ml (0.3 mol) of tert-butyl chloroacetate in 100 ml of dichloromethane were added dropwise to the thoroughly stirred solution within the space of approx. 2.5 h. The reaction was slightly exothermic. After approx. 15 min, the mixture became turbid and the diamine hydrochloride which had been formed settled out as an oily phase. The reaction mixture was then stirred at room temperature for about another 2 h in order to complete the reaction (monitoring by TLC in ethyl methyl ketonelpyridine/water/glacial acetic acid 70:15:15:2), and 200 ml of water were then added to it. The organic phase was separated off and the aqueous phase was extracted a further two times with 100 ml of dichloromethane on each occasion. The combined organic phases were then back-extracted once again with 100 ml of water and dried over sodium sulfate. After the drying agent had been filtered off, the organic phase was made up to 800 ml, and 40 ml were concentrated to dryness in order to determine the crude yield. Residue, 2.28 g, which corresponds to a total quantity of 45.6 g (86%). This dichloromethane solution of the crude product was then directly subjected to further reaction, as described below, in order to form Boc-Aeg-OtBu. MS(ES$^+$): 189.1 (M+H)$^+$ $R_f$=0.36 (2-butanone:water:pyridine:acetic acid/ 70:15:15:2)

Step 2:

38 ml (0.27 mol) of triethylamine were added to 0.26 mol of H-Aeg-OtBu (solution in 800 ml of dichloromethane), after which a solution of 54.5 g (0.25 mol) of di-tert-butyl dicarbonate in 100 ml of dichloromethane was slowly added dropwise, within the space of 45 min, while the mixture was being thoroughly stirred. In association with this, the reaction solution became more viscous due to the carbamate (from $CO_2$) which was formed and was therefore diluted with 100 ml of dichloromethane. After the reaction had finished, the solution was of low viscosity and was only slightly turbid. 100 ml of water were added, the organic phase was separated off and the aqueous phase was extracted once again with 100 ml of dichloromethane. The organic phase was dried over sodium sulfate and then concentrated in vacuo. Crude product: 77.6 g of a colorless oil. This crude product was purified by column chromatography on silica gel using ethyl acetate as the eluent. Yield: 48.1 g.

MS(ES$^+$): 275.2 (M+H)$^+$ $R_f$=0.46 (ethyl acetate)

Example 12

N-(tert-Butyloxycarbonylaminoethyl)-N-((1-thyminyl) acetyl)glycine tert-butyl ester Boc-Aeg(T)-OtBu 1.375 g (5 mmol) of Boc-Aeg-OtBu were dissolved in 20 ml of DMF, after which 921 mg (5 mmol) of thyminylacetic acid, 1.64 g (5 mmol) of TOTU and 1.7 ml (10 mmol) of diisopropylethylamine were added in succession. The mixture was stirred at room temperature overnight and then evaporated in vacuo. The oily residue was taken up in 70 ml of ethyl acetate, and this solution was extracted in each case 5 times with 5 ml on each occasion of sodium hydrogen carbonate solution and potassium hydrogen sulfate solution. It was then washed a further three times with 5 ml of water on each occasion. The organic phase was dried over sodium sulfate and then concentrated down to dryness. The solid residue which remained was triturated with diethyl ether, filtered off with suction and dried. Yield: 1.82 g.

MS(ES$^+$): 441.3 (M+H)$^+$ $R_f$=0.55 (dichlormethane:methanol:triethylamine/ 100:10:1)

Example 12a

N-(tert-Butyloxycarbonylaminoethyl)-N-((1-thyminyl) acetyl)glycine tert-butyl ester Boc-Aeg(T)-OtBu 6.875 g (25 mmol) of Boc-Aeg-OtBu were dissolved in 100 ml of DMF, after which 4.6 g (25 mmol) of thyminylacetic acid, 8.2 g (25 mmol) of TOTU and 8.5 ml (100 mmol) of diisopropylethylamine were added in succession. The mixture was stirred at room temperature for 4h and then evaporated in vacuo. The oily residue was taken up in 350 ml of ethyl acetate, and this solution was extracted in each case 5 times with 5 ml on each occasion of sodium hydrogen carbonate solution and potassium hydrogen sulfate solution. It was then washed a further three times with 5 ml of water on each occasion. In association with this, material already precipitated out in the organic phase and was filtered off with suction. The organic phase of the filtrate was separated off, dried over sodium sulfate and then concentrated to dryness. The solid residue which remained was triturated with diethyl ether, filtered off with suction and dried. The pooled crude products were recrystallized from ethyl acetate.

Yield: 9.71 g.

MS(ES$^+$): 441.3 (M+H)$^+$ $R_f$=0.55 (dichloromethane:methanol:triethylamine/ 100:10:1)

Example 13

N-(tert-Butyloxycarbonylaminoethyl)-N-((1-(N$^4$-(4-methoxybenzoyl)cytosyl)acetyl)glycine tert-butyl ester Boc-Aeg(C$^{MeBz}$)-OtBu 1.375 g (5 mmol) of Boc-Aeg-OtBu were dissolved in 20 ml of DMF, after which 1.515 g (5 mmol) of N$^4$-(4-methoxybenzoyl)-N$^1$-carboxymethylcytosine, 1.64 g (5 mmol) of TOTU and 1.7 ml (10 mmol) of diisopropylethylamine were added in succession. The mixture was stirred at room temperature overnight and then evaporated in vacuo. The semisolid residue was taken up in dichloromethane, and this solution was filtered and the filtrate was concentrated. The residue was triturated with ethyl acetate, whereupon the product precipitated out as a solid substance. It was recrystallized from a little ethyl acetate, filtered off with suction, washed with ethyl acetate and dried in vacuo.

Yield: 1.89 g

MS(ES$^+$): 560.3 (M+H)$^+$ $R_f$=0.53 (dichloromethane:methanol:triethylamine/ 100:10:1)

Example 14

N-(tert-Butyloxycarbonylaminoethyl)-N-((9-(N$^6$4-methoxybenzoyl)adenosyl)acetyl)glycine tert-butyl ester Boc-Aeg(A$^{MeBz}$)-OtBu 549 mg (2 mmol) of Boc-Aeg-OtBu were dissolved in 10 ml of DMF, after which 655 mg (2 mmol) of N$^6$-4-(methoxybenzoyl)-N$^9$-carboxymethyladenine, 656 mg (2 mmol) of TOTU and 0.68 ml (4 mmol) of diisopropylethylamine were added in succession. The mixture was stirred at room temperature overnight and then evaporated in vacuo. The residue was taken up in 30 ml of ethyl acetate, and this solution was washed in each case twice with 5 ml, on each occasion, of sodium hydrogen carbonate solution and of water. The organic phase was dried over sodium sulfate and then concentrated down to dryness. The solid residue which remained was triturated with diethyl ether, filtered off with suction and dried. Yield: 730 mg.

MS(FAB, MeOHINBA): 584.2 (M+H)$^+$ $R_f$=0.74 (dichloromethane:methanol/10:1 and 1% triethylamine)

Example 15

N-(Amino)ethyl-N-((1-thyminyl)acetyl)glycine (H-Aeg(T)-OH)

110 ml of 95% trifluoroacetic acid (5% water) were added to 11.0 g (25 mmol) of Boc-Aeg(T)-OtBu. A clear solution was formed which was stirred at room temperature for 2h. The reaction mixture was then concentrated and the residue was triturated with diethyl ether. The precipitated crude product was used directly for the next step in the synthesis.

Yield: 7.1 g of an amorphous solid

MS(ES$^+$): 285.2 (M+H)$^+$

R$_f$=0.14 (2-butanone:water:pyridine:acetic acid/ 70:15:15:2)

Example 16

N-((4-Methoxyphenyl)diphenylmethylamino)ethyl-N-((1-thyminyl)acetyl) glycine (Mmt-Aeg(T))-OH 7.1 g of H-Aeg(T)-OH from the previous reaction were dissolved in 300 ml of DMF, after which 13.9 ml (100 mmol) of triethylamine were added, followed by 8.9 g (29.2 mmol) of Mmt-Cl in 5 portions. The mixture was stirred overnight, after which undissolved material (unreacted H-Aeg(T)-OH, 2.78 g) was removed by filtration and the filtrate was evaporated in vacuo. The residue was taken up in 300 ml of dichloromethane, and this solution was washed three times with 30 ml of water. The organic phase was dried over sodium sulfate and then concentrated down to dryness. The solid residue which remained was dissolved in a little ethyl acetate, after which a little triethylamine was added and the whole was stirred into 200 ml of diethyl ether. The precipitated product was filtered off with suction, washed with a little ether, and dried in vacuo.

Yield: 7.3 g

MS(FAB, MeOH/NBA/LiCl): 569.5 (M+Li)$^+$

R$_f$=0.25 (dichloromethane:methanol:triethylamine/ 100:10:1)

Example 17

N-(Amino)ethyl-N-((1-(N$^4$-(4-methoxybenzoyl)cytosyl) acetyl)glycine (H-Aeg(C$^{MeBz}$)-OH)

A mixture comprising 30 ml of dichloromethane and 16 ml of 95% trifluoroacetic acid (5% water) was added to 1.6 g (2.9 mmol) of Boc-Aeg(C$^{MeBz}$)-OtBu. A clear solution was formed which was stirred at room temperature for 3 h. The reaction mixture was then concentrated and the residue was triturated with diethyl ether. The precipitated crude product was used directly for the next step of the synthesis.

Yield: 1.86 g of an amorphous solid substance

R$_f$=0.34 (2-butanone:water:pyridine:acetic acid/ 70:15:15:2)

Example 18

N-((4-Methoxyphenyl)diphenylmethylamino)ethyl-N-((1-(N$^4$-(4-methoxybenzoyl)cytosyl)acetyl)glycine (Mmt-Aeg(C$^{MeBz}$))-OH 1.26 g of H-Aeg(C$^{MeBz}$)-OH from the previous reaction were dissolved in 50 ml of DMF, after which 2.1 ml (15 mmol) of triethylamine were added, followed by 1.06 g (3.5 mmol) of Mmt-Cl in 3 portions. The mixture was stirred overnight, after which a little undissolved material was removed by filtration and the filtrate was evaporated in vacuo. The residue was taken up in 50 ml of dichloromethane, and this solution was washed three times with 10 ml of water. The organic phase was dried over sodium sulfate and then concentrated down to approx. 10 ml; the latter was then stirred into 80 ml of diethylether. The precipitated product was filtered off with suction, washed with a little ether, and dried in vacuo.

Yield: 1.35 g

MS(FAB, MeOH/NBA): 676.4 (M+H)$^+$

R$_f$=0.62 (2-butanone:water:pyridine:acetic acid/ 70:15:15:2)

Example 19

N-(Amino)ethyl-N-((9-(N$^6$-4-methoxybenzoyl)adenosyl) acetyl)glycine (H-Aeg(A$^{MeBz}$)-OH)

10 ml of 95% trifluoroacetic acid (5% water) were added to 725 mg (1.2 mmol) of Boc-Aeg(A$^{MeBz}$)-OtBu. A clear solution was formed which was stirred at room temperature for 3 h. The reaction mixture was then concentrated, and the residue was triturated with diethyl ether. The precipitated crude product was used directly for the next step of the synthesis.

Yield: 830 mg of an amorphous solid substance.

Example 20

N-((4-Methoxyphenyl)diphenylmethylamino)ethyl-N-((9-(N$^6$4-methoxybenzoyl)adenosyl)acetyl)glycine (Mmt-Aeg(A$^{MeBz}$))-OH 690 mg of H-Aeg(A$^{MeBz}$)-OH from the previous reaction were dissolved in 25 ml of DMF, after which 0.88 ml (6.5 mmol) of triethylamine were added, followed by 494 mg (1.6 mmol) of Mmt-Cl in 3 portions. The mixture was stirred overnight, after which a little undissolved material was removed by filtration and the filtrate was evaporated in vacuo. The residue was taken up in 20 ml of dichloromethane, and this solution was washed three times with 5 ml of water. The organic phase was dried over sodium sulfate and then concentrated, and the residue was triturated with diethyl ether. The precipitated product was filtered off with suction, washed with a little ether and dried in vacuo.

Yield: 440 mg

MS(ES$^+$): 700.3 (M+H)$^+$

R$_f$=0.59 (2-butanone:water:pyridine:acetic acid/ 70:15:15:2)

Example 21

N-(tert-Butyloxycarbonylaminoethyl)-N-((9-(N$^2$-acetyl-O$^4$-diphenylcarbamoyl)guanosyl)acetyl)glycine tert-butyl ester Boc-Aeg(G$^{2-Ac,4-Dpc}$)-OtBu 1.375 g (5 mmol) of Boc-Aeg-OtBu were dissolved in 30 ml DMF, after which 2.23 g (5 mmol) of $^{N2}$-acetyl-O$^4$-diphenylcarbamoyl-9-carboxy methylguanine, 1.64 g (5 mmol) of TOTU and 1.7 ml (10 mmol) of diisopropylethylamine were added in succession. The mixture was stirred at room temperature overnight and then evaporated in vacuo. The residue was taken up in 50 ml of ethyl acetate, and this solution was extracted in each case 4 times with 3 ml of sodium hydrogen carbonate solution, 3 ml of potassium hydrogen sulfate solution and 3 ml of water. The organic phase was dried over sodium sulfate, and the drying agent was then removed by filtration and the filtrate was concentrated. The residue was triturated with ether, in association with which the product remained behind as a resinous solid substance. This product was used for the subsequent reaction without any further purification.

Yield: 3.14 g

MS(FAB, NBA/MeOH): 703.3 (M+H)$^+$

R$_f$=0.80 (dichloromethane:methanol:triethylamine/ 100:10:1)

Example 22

N-(Aminoethyl)-N-((9-(N$^2$-acetyl)guanosyl)acetyl) glycine

H-Aeg(G$^{2\text{-}Ac}$)-OH 20 ml of 95% trifluoroacetic acid (5% water) were added to 2.08 g (2.96 mmol) of Boc-Aeg (G$^{2\text{-}Ac,4\text{-}DPc}$)-OtBu. A clear solution was formed which was stirred at room temperature for 30 min. The reaction mixture was then concentrated, and the residue was triturated with diethyl ether. The precipitated crude product was used directly for the next step of the synthesis.

Yield: 1.46 g of an amorphous solid substance

R$_f$=0.15 (2-butanone:water:pyridine:acetic acid/ 70:15:15:2)

Example 23

Mmt-Aeg(G$^{2\text{-}Ac}$)-OH 1.46 g H-Aeg (G$^{2\text{-}Ac}$)-OH from the previous reaction were dissolved in 30 ml of DMF, after which 2.1 ml (15 mmol) of triethylamine were added, followed by 939 mg (3.04 mmol) of Mmt-Cl in 3 portions. The mixture was stirred overnight, after which a little undissolved material was removed by filtration and the filtrate was evaporated in vacuo. The residue was taken up in 30 ml of ethyl acetate, and this solution was extracted in each case 3 times with 3 ml of sodium hydrogen carbonate solution and 3 ml of water. The organic phase as dried over sodium sulfate, the drying agent was filtered off and the filtrate was concentrated. The residue was triturated with ether. The precipitated product was filtered off with suction, washed with a little ether and dried in vacuo.

Yield: 1.10 g

MS(ES$^+$): 624.3 (M+H)$^+$

R$_f$=0.14 (dichloromethane:methanol:triethylamine/ 100:10:1)

Example 24

N-(tert-Butyloxycarbonylaminoethyl)-N-((1-(N$^4$-(4-methoxybenzoyl)cytosyl)acetyl)glycine tert-butyl ester Boc-Aeg(C$^{MeOBz}$)-OtBu 1.5 l of ethyl acetate were added to 114.6 g (0.418 mol) of Boc-Aeg-OtBu and 127 g (0.418 mol) of N4-(4-methoxybenzoyl)-N$^1$-carboxymethylcytosine, and 115 ml (0.836 mol) of triethylamine were added to the stirred suspension. 400 ml (approx. 0.628 mol) of a 50% solution of propylphosphonic anhydride in ethyl acetate were then added within the space of 2 min. In association with this, the temperature rose slightly. The mixture was adjusted to pH 8 by adding a further 65 ml (0.469 mol) of triethylamine and then stirred for a further 2.5h. The precipitate was filtered off with suction and washed firstly with 500 ml of ethyl acetate and then with 1 l of water. Further product precipitated out of the mother liquor. Both precipitates were stirred once again with 500 ml of water, then filtered off with suction, washed with 500 ml of water and dried in vacuo.

Yield: 196.6 g

Example 25

N-(tert-Butyloxycarbonylaminoethyl)-N-((9-( N$^6$-4-methoxybenzoyl)adenosyl)acetyl)glycine tert-butyl ester Boc-Aeg(A$^{MeOBz}$)-OtBu 300.0 g (1.094 mol) of Boc-Aeg-OtBu were dissolved in 2.8 l of DMF, after which 358.2 g (1.094 mol) of N$^6$-(4-methoxybenzoyl)-N$^9$-carboxymethyladenine, 360.5 g (2 mmol) of TOTU and 373.9 ml (2.184 mol) of diisopropyl-ethylamine were added in succession. The mixture was stirred at room temperature for a further 2h and then added dropwise to a stirred, ice-cooled solution of 214.29 g of sodium hydrogen carbonate in 2.2 l of water, whereupon the product precipitated out. A further 2 l of methyl tert-butyl ether were then added. This mixture was left to stand overnight. The precipitate was then filtered off with suction and stirred up, in succession, with two times 2 l of water and two times 2 l of methyl tert-butyl ether; the precipitate was then filtered off once again and dried in vacuo. Yield: 437.7 g.

Example 26

N-(tert-Butyloxycarbonylaminoethyl)glycine tert-butyl ester

Boc-Aeg-OtBu

Step 1:N-Boc-1,2-diaminoethane 535 ml (8 mol) of 1,2-diaminoethane were dissolved in 2 l of dichloromethane. A solution of 218.5 g (1 mol) of di-tert-butyl dicarbonate in 500 ml of dichloromethane was added dropwise, while stirring and cooling, within the space of 1.5 h. The mixture was then stirred for a further 20 h, after which 1 l of water was added and the resulting mixture was stirred vigorously. The phases were separated and the aqueous phase was extracted a further two times with 500 ml of dichloromethane on each occasion. The combined organic phases were washed with a half-saturated solution of sodium chloride and dried over sodium sulfate. The organic phase was concentrated down to a volume of 1 l.

Step 2: Boc-Aeg-OtBu 138 ml (0.97 mol) of triethylamine and a spatula tip (about 0.1 g,) of potassium iodide were added to the solution obtained above. A solution of 149.5 ml of tert-butyl chloroacetate was then added dropwise while stirring, and this mixture was stirred at 40° C. for 50 h. 500 ml of water were then added and the mixture was agitated vigorously; the organic phase was then separated off, dried over sodium sulfate and concentrated. The resulting crude product was purified on silica gel using ethyl acetate/methanol 95:5 as the eluent. 78 g of the desired product were obtained.

Example 27

N-(tert-Butyloxycarbonylaminoethyl)glycine tert-butyl ester

Boc-Aeg-OtBu

Step 1:N-Boc-1,2-diaminoethane 4.8 l (72 mol) of 1,2-diaminoethane were dissolved in 18 l of dichloromethane. A solution of 1.97 kg (9.03 mol) of di-tert-butyl dicarbonate in 4.5 l of dichloromethane was added dropwise, while stirring and cooling, within the space of 2 h. The mixture was then stirred for a further 20 h, after which 9 l of water were added and the resulting mixture was agitated vigorously. The phases were separated and the aqueous phase was extracted a further two times with 4.5 l of dichloromethane on each occasion. The combined organic phases were washed with a half-saturated solution of sodium chloride and dried over sodium sulfate. The organic phase was concentrated down to a volume of 9 l.

Step 2: Boc-Aeg-OtBu 1.24 l of triethylamine and 5 g of potassium iodide were added to the solution obtained above. A solution of 1.245 l of tert-butyl chloroacetate in 4.5 l of dichloromethane was then added dropwise while stirring, and this mixture was stirred at 40° C. for 50 h. 5 l of water were then added and the mixture was agitated vigorously; the organic phase was then separated off, dried over sodium sulfate and concentrated. The resulting crude product was chromatographically purified on silica gel using ethyl acetate/methanol 95:5 as the eluent. 1.03 kg of the desired product were obtained.

Further abbreviations employed are listed below.

| | |
|---|---|
| Aeg | N-(2-Aminoethyl)glycyl, —NH—$CH_2$—$CH_2$—NH—$CH_2$—CO— |
| Aeg($A^{MeOBz}$) | N-(2-Aminoethyl)-N-((9-($N^6$-4-methoxybenzoyl)-adenosyl)acetyl)glycyl |
| Aeg($C^{Bz}$) | N-(2-Aminoethyl)-N-((1-($N^4$-benzoyl)-cytosyl)acetyl)glycyl |
| Aeg($C^{MeOBz}$) | N-(2-Aminoethyl)-N-((1-($N^4$-4-methoxybenzoyl)-cytosyl)acetyl)glycyl |
| Aeg($C^{tBuBz}$) | N-(2-Aminoethyl)-N-((1-($N^4$-4-tert-butylbenzoyl)-cytosyl)acetyl)glycyl |
| Aeg($G^{iBu}$) | N-(2-Aminoethyl)-N-((9-($N^2$-isobutanoyl)guanosyl)acetyl)glycyl |
| Aeg($G^{2\text{-}Ac,4\text{-}Dpc}$) | N-(2-Aminoethyl)-N-((9-($N^2$-acetyl-$O^4$-diphenylcarbamoyl)guanosyl)acetyl)glycyl |
| Aeg($G^{2\text{-}Ac}$) | N-(2-Aminoethyl)-N-((9-($N^2$-acetyl)guanosyl)acetyl)glycyl |
| Aeg(T) | N-(2-Aminoethyl)-N-((1-thyminyl)acetyl)glycyl |
| Bnpeoc | 2,2-[Bis(4-nitrophenyl)]-ethoxycarbonyl |
| Boc | tert-Butyloxycarbonyl |
| BOI | 2-(Benzotriazol-1-yl)oxy-1,3-dimethylimidazolidinium hexafluorophosphate |
| BOP | Benzotriazolyl-1-oxy-tris(dimethylamino)phosphonium hexafluorophosphate |
| BroP | Brom-tris(dimethylamino)phosphonium hexafluorophosphate |
| BSA | N,O-Bis-(trimethylsilyl)acetamide |
| But | tert-Butyl |
| Bz | Benzoyl |
| Bzl | Benzyl |
| Cl-Z | 4-Chlorobenzyloxycarbonyl |
| CPG | Controlled pore glass |
| DBU | 1,8-diazabicyclo[5.4.0]undec-7-ene |
| DCM | Dichloromethane |
| Ddz | 3,5-Dimethoxyphenyl-2-propyl-2-oxycarbonyl |
| DMF | Dimethylformamide |
| Dmt | Di-(4-methoxyphenyl)phenylmethyl, |
| Dnpeoc | 2-(2,4-Dinitrophenyl)ethoxycarbonyl |
| Dpc | Diphenylcarbamoyl |
| FAM | Fluorescein residue |
| Fm | 9-Fluorenylmethyl |
| Fmoc | 9-Fluorenylmethyloxycarbonyl |
| H-Aeg-OH | N-(2-Aminoethyl)glycine |
| HAPyU | O-(7-Azabenzotriazol-1-yl)-1,1,3,3-bis(tetramethylene)-uronium hexafluorophosphate |
| HATU | O-(7-Azabenzotriazol-1-yl)-1,1,3,3-tetramethyluronium hexafluorophosphate |
| HBTU | O-(Benzotriazol-1-yl)-1,1,3,3-tetramethyluronium hexafluorophosphate |
| HOBt | 1-Hydroxybenzotriazole |
| HONSu | N-Hydroxysuccinimide |
| HOObt | 3-Hydroxy-4-oxo-3,4-dihydrobenzotriazine |
| iBu | Isobutanoyl |
| MeOBz | 4-Methoxybenzoyl |
| Mmt | 4-Methoxytriphenylmethyl |
| Moz | 4-Methoxybenzyloxycarbonyl |
| MSNT | 2,4,6-Mesitylenesulfonyl-3-nitro-1,2,4-triazolide |
| Mtt | 4-Methylphenyl)diphenylmethyl |
| NMP | N-Methylpyrrolidine |
| Oeg | N-(2-Oxyethyl)glycyl, —O—$CH_2$—$CH_2$—NH—$CH_2$—CO— |
| Pixyl | 9-(9-Phenyl)xanthenyl |
| PyBOP | Benzotriazolyl-1-oxy-tripyrrolidinophosphonium hexafluorophosphate |
| PyBroP | Bromotripyrrolidinophosphonium hexafluorophosphate |
| TAPipU | O-(7-Azabenzotriazol-1-yl)-1,1,3,3-bis(pentamethylene)-uronium tetrafluoroborate |
| TBTU | O-(Benzotriazol-1-yl)-1,1,3,3-tetramethyluronium tetrafluoroborate |
| tBu | tert-Butyl |
| tBuBz | 4-tert-Butylbenzoyl |
| TDBTU | O-(3,4-Dihydro-4-oxo-1,2,3-benzotriazin-3-yl)-1,1,3,3-tetramethyluronium tetrafluoroborate |
| TDO | 2,5-Diphenyl-2,3-dihydro-3-oxo-4-hydroxythiophene dioxide |
| TFA | Trifluoroacetic acid |
| THF | Tetrahydrofuran |
| TNTU | O-(5-Norbonene-2,3-dicarboximido)-1,1,3,3-tetramethyl-uronium tetrafluoroborate |
| TOTU | O-[(Cyano(ethoxycarbonyl)methylen)amino]-1,1,3,3-tetramethyluronium tetrafluoroborate |
| TPTU | O-(1,2-Dihydro-2-oxo-1-pyridyl)-1,1,3,3'-tetramethyl-uronium tetrafluoroborate |
| Trt | Trityl |
| TSTU | O-(N-Succinimidyl)-1,1,3,3-tetramethyluronium tetrafluoroborate |
| Z | Benzyloxycarbonyl |
| MS($ES^+$) | Electrospray mass spectrum (positive ion) |
| MS($ES^-$) | Electrospray mass spectrum (negative ion) |
| MS(DCI) | Direct-ionization mass spectrum |
| MS(FAB) | Fast-atom-bombardment mass spectrum |
| NBA | Nitrobenzyl alcohol |

What is claimed is:

1. A process for preparing a substituted N-ethylglycine derivative of the formula I

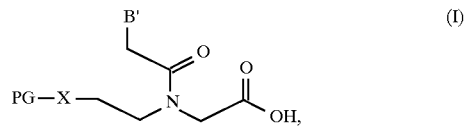

in which

PG is a protecting group which is labile towards weak acids,

X is NH or O, and

B' is a nucleotide base wherein any exocyclic amino or hydroxyl group is protected by a protecting group, or a salt thereof, which comprises, a) reacting a compound of the formula II

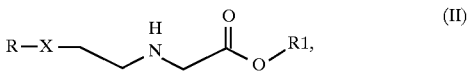

in which

X is defined as above,

R is hydrogen or, when X=NH, R is an acid-labile protecting group, and $R^1$ is a protecting group which is labile towards acids and stable towards amines, with a compound of the formula III

in which

B' is defined as above, at 0°–45° C. in a solvent using a coupling reagent to give a compound of the formula IV

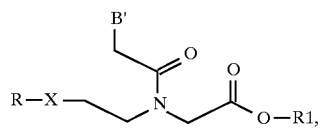 (IV)

in which

R, X, B' and $R^1$ are defined as above;

b) converting the compound of the formula IV into a compound of the formula V, by eliminating the acid-labile ester protecting group $R^1$ and, when X=NH, by simultaneously eliminating the acid-labile protecting group R under acidic conditions, in a solvent, where appropriate, with the addition of a cation-capturing agent, and when X=O, where appropriate, additionally treating with a base in aqueous medium,

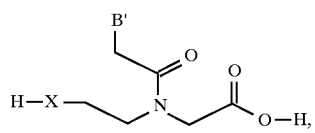 (V)

in which

X and B' are defined as above; and c) converting the compound of the formula V into the compound of the formula I, by introducing therein the protecting group PG, using a reagent in a solvent and using an auxiliary base.

2. The process for preparing a substituted N-ethylglycine derivative of the formula I as claimed in claim 1, wherein PG is protecting group which is a urethane derivative or a triphenylmethyl derivative.

3. The process for preparing a substituted N-ethylglycine derivative of the formula I as claimed in claim 1, which further comprises converting the resulting compound of the formula I into one of its salts.

4. The process for preparing a substituted N-ethylglycine derivative of the formula I

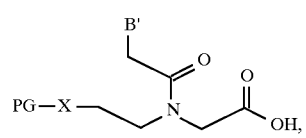 (I)

wherein

PG is a protecting group which is labile towards weak acids,

X is NH or O, and

B' is a nucleotide base wherein any exocyclic amino or hydroxyl group is protected by a protecting group, or a salt thereof comprising a) reacting a compound of the formula II

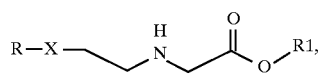 (II)

in which

R is hydrogen, or, when X=NH, R is Boc, Ddz or Trt and, $R^1$ is tert-butyl or (2-chlorophenyl)diphenylmethyl, with a compound of the formula III

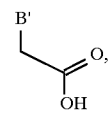 (III)

in which

B' is a nucleotide base wherein any exocylic amino or hydroxyl group is protected by a protecting group, at room temperature, in DMF, acetonitrile, dichloromethane or a mixture of these solvents, using a carbodiimide, phosphonium reagent, uronium reagent, acid halide or activated ester, to give a compound of the formula IV

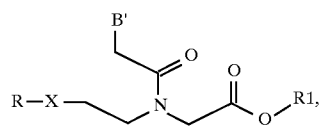 (IV)

in which R, X, B' and $R^1$ are defined as above;

b) converting the compound of the formula IV, by eliminating the acid-labile ester protecting group $R^1$ and, when X=NH, by simultaneously eliminating the acid-labile protecting group R with trifluoroacetic acid in dichloromethane, ethyl acetate or dioxane, where appropriate, with the addition of anisole, thiophenol or triethylsilane, into a compound of the formula V

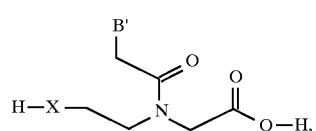 (V)

in which

X and B' are defined as above, and when X=O additionally treating, where appropriate, with NaOH or triethylamine in aqueous medium; and c) converting the compound of the formula V into the compound of the formula I, with t-Bumeoc fluoride Adpoc azide, Bpoc azide, Ddz-(phenyl)carbonate, Trt-Cl, Mtt-Cl, Mmt-Cl, Dmt-Cl or Pixyl-Cl in DMF, NMP, acetonitrile, dichloromethane or a mixture of these solvents, using NEM, DIPEA, pyridine or triethylamine.

5. The process for preparing a substituted N-ethylglycine derivative of the formula I as claimed in claim 4, which further comprises converting the resultant compound of the formula I into one of its salts.

6. The process for preparing substituted N-ethylglycine derivatives of the formula I as claimed in claim 4, wherein, in the compound of the formula II, R is hydrogen or, when X=NH, R is Boc, and $R^1$ is tert-butyl.

7. An intermediate of the formula IV

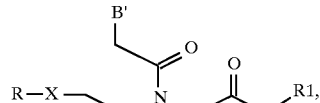 (IV)

in which

X is NH or O,

B' is a nucleotide base wherein any exocyclic amino or hydroxyl group is protected by a protecting group, R is hydrogen or, when X=NH, R is an acid-labile protecting group, and $R^1$ is a protecting group which is labile towards acids and stable towards amines.

8. A process for preparing a substituted N-ethylglycine derivative of the formula I or salt thereof as claimed in claim 1, wherein B' is selected from adenine, cytosine, guanine, thymine and uracil, or purine, 2,6-diaminopurine, 7-deazaadenine or 7-deazaguanine, $N^4N^4$-ethanocytosine, $N^6N^6$-ethano-2,6-diaminopurine, 5-methylcytosine, 5-($C_3$–$C_6$)-alkynyluracil, 5-($C_3$–$C_6$)-alkynylcytosine, 5-fluorouracil, and pseudoisocytosine, and wherein any exocyclic amino or hydroxyl group of said nucleotide base is protected by a protecting group.

9. A process for preparing a substituted N-ethylglycine derivative of the formula I or salt thereof as claimed in claim 8, wherein B' is 7-deazaadenine or 7-deazaguanine, and wherein said 7-deazaadenine or said 7-deazaguanine is substituted in the 7-position by a substituent selected from halogen, ($C_1$–$C_{10}$)-alkyl, ($C_2$–$C_{10}$)-alkenyl, ($C_3$–$C_{10}$)-alkynyl, ($C_3$–$C_6$)-alkyl, ($C_3$–$C_6$)-alkenyl, and ($C_3$–$C_{10}$)-alkynyl.

10. A process for preparing a substituted N-ethylglycine derivative of the formula I or salt thereof as claimed in claim 8, wherein said exocyclic amino or hydroxy group of said nucleotide base is protected by a protecting group selected from benzoyl, isobutanoyl, acetyl, phenoxyacetyl, 4-(t-butyl)benzoyl, 4-(t-butyl)phenoxyacetyl, 4-(methoxy)benzoyl, 2-(4-nitrophenyl)ethyloxycarbonyl, 2-(2,4-dinitrophenyl)ethyloxycarbonyl, 9-fluorenylmethoxycarbonyl diphenylcarbamoyl and formamidine.

11. A process for preparing a substituted N-ethylglycine derivative of the formula I or salt thereof as claimed in claim 8, wherein B' is guanine, and wherein said guanine is protected by a combination of 2-N-acetyl and 6-O-diphenylcarbamoyl groups.

12. The process for preparing a substituted N-ethylglycine derivative of the formula I or salt thereof as claimed in claim 2, wherein said urethane derivative is selected from 1-(1 adamantyl)-1-methyl-ethoxycarbonyl (Adpoc), 1-(3,5-di-tert-butylphenyl)-1-methylethoxy-carbonyl (t-Bumeoc), 1-methyl-1-(4-biphenyl)ethoxycarbonyl (Bpoc), tert-butylcarbonyl (Boc) and 3,5-dimethoxyphenyl-2-propyloxycarbonyl (Ddz).

13. The process for preparing a substituted N-ethylglycine derivative of the formula I or salt thereof as claimed in claim 2, wherein said triphenylmethyl derivative is selected from triphenylmethyl (Trt), (4-methoxyphenyl)diphenylmethyl (Mmt), (4-methylphenyl)diphenylmethyl (Mtt), di-(4-methoxyphenyl)phenylmethyl (Dmt), and 9-(9-phenyl)xanthenyl (pixyl) radical.

14. A process as claimed in claim 1, wherein said weak acid is trifluoroacetic acid.

15. An intermediate of the formula IV or salt thereof as claimed in claim 7, wherein R is hydrogen, or, when X=NH, R is Boc, Ddz or Trt, and $R^1$ is a protecting group which is labile towards acids and stable towards amines.

* * * * *

UNITED STATES PATENT AND TRADEMARK OFFICE
CERTIFICATE OF CORRECTION

PATENT NO. : 5,817,811
DATED : October 6, 1998
INVENTOR(S) : Breipohl et al.

It is certified that error appears in the above-identified patent and that said Letters Patent is hereby corrected as shown below:

Title Page, Item [54], in the Title, line 2, "N-ETHYGLYCINE" should read --N-ETHYLGLYCINE--., and col. 1, line 2.
Claim 1, column 16, line 42, after "comprises", delete ",".
Claim 2, column 17, line 34, before "protecting", insert --a--.

Signed and Sealed this

Fourteenth Day of December, 1999

Attest:

Attesting Officer

Q. TODD DICKINSON

Acting Commissioner of Patents and Trademarks